United States Patent [19]

Bertram

[11] Patent Number: 4,474,943

[45] Date of Patent: Oct. 2, 1984

[54] PHOSPHORAMIDE EPOXY RESINS

[75] Inventor: James L. Bertram, Lake Jackson, Tex.

[73] Assignee: The Dow Chemical Company, Midland, Mich.

[21] Appl. No.: 516,829

[22] Filed: Jul. 25, 1983

[51] Int. Cl.³ .................. C08G 59/30; C08G 59/28
[52] U.S. Cl. .................... 528/365; 549/219; 528/399
[58] Field of Search ............... 528/399, 365; 549/219

[56] References Cited

U.S. PATENT DOCUMENTS

| | | | |
|---|---|---|---|
| 2,939,849 | 6/1960 | Frick et al. | 528/399 |
| 3,281,502 | 10/1966 | Pelletier et al. | 524/219 X |
| 3,516,965 | 6/1970 | Washburn | 260/47 |
| 3,933,738 | 1/1976 | Murch et al. | 260/45.9 NP |
| 4,164,487 | 8/1979 | Martin | 260/29.2 EP |
| 4,316,922 | 2/1982 | Perine et al. | 428/35 |

Primary Examiner—Earl A. Nielsen
Attorney, Agent, or Firm—J. G. Carter

[57] ABSTRACT

Epoxy resins are disclosed which are the dehydrohalogenated reaction products of an epihalohydrin and a phosphoramide.

10 Claims, No Drawings

PHOSPHORAMIDE EPOXY RESINS

BACKGROUND OF THE INVENTION

The present invention concerns epoxy resins prepared from phosphoramide materials and cured compositions thereof.

Epoxy resins have been cured with phosphoramide compounds thereby putting phosphorus atoms in the backbone of the cured product. The present invention places phosphorus atoms into the backbone via the epoxy resin rather than the curing agent thereby providing for a varying range of properties by providing a choice of curing agents rather than a choice of epoxy resin.

SUMMARY OF THE INVENTION

The present invention concerns an epoxy resin which results from dehydrohalogenating the reaction product of an excess of at least one epihalohydrin with at least one phosphoramide compound represented by the formula

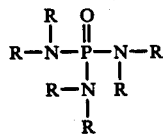

wherein each R is independently hydrogen or a hydrocarbyl or an inert substituted hydrocarbyl group having from 1 to about 20, preferably from 1 to about 10, carbon atoms, with the proviso that at least 2 of the R groups are hydrogen and removing the excess epihalohydrin. The term hydrocarbyl means a monovalent organic hydrocarbon group. The term inert substituted means that the hydrocarbon group can contain substituent groups which do not interfere with the reaction with an epihalohydrin or the subsequent dehydrohalogenation reaction. Such substituents include, for example, aryloxy, alkoxy, hydroxyalkyl, chlorine, bromine and the like.

Another aspect of the present invention concerns an epoxy resin represented by the formula

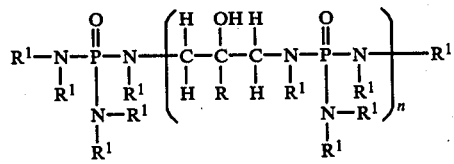

wherein each R is independently hydrogen or an alkyl group having from about 1 to about 4 carbon atoms; each $R^1$ is independently a hydrocarbyl or an inert substituted hydrocarbyl group having from 1 to about 20, preferably from 1 to about 10 carbon atoms or

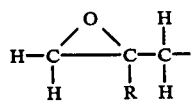

with the proviso that at least 2 of the $R^1$ groups are

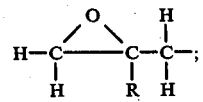

and n has an average value of from zero to about 10, preferably from zero to about 2.

The present invention also concerns curable compositions containing the aforementioned epoxy resins and, a curing quantity of one or more suitable curing agents.

Further, the present invention concerns cured compositions resulting from subjecting the aforementioned curable composition to curing conditions.

DETAILED DESCRIPTION OF THE PRESENT INVENTION

Suitable epihalohydrins which can be employed herein include those represented by the formula

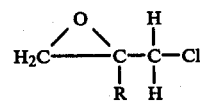

wherein R is an alkyl group having from 1 to about 4 carbon atoms.

Particularly suitable epihalohydrins include, for example, epichlorohydrin, epibromohydrin, epiiodohydrin, methylepichlorohydrin, methylepibromohydrin, methylepiiodohydrin, mixtures thereof and the like.

Particularly suitable phosphoramides include, for example, methylphosphoramide, dimethylphosphoramide, trimethylphosphoramide, ethylphosphoramide, diethylphosphoramide, triethylphosphoramide, propylphosphoramide, dipropylphosphoramide, tripropylphosphoramide, butylphosphoramide, dibutylphosphoramide, tributylphosphoramide, phenylphosphoramide, diphenylphosphoramide, triphenylphosphoramide, mixtures thereof and the like.

The reaction between the eiphalohydrin and the phosphoramide is usually, but not necessarily, conducted in the presence of a catalyst. Suitable catalysts include quaternary ammonium compounds, phosphonium compounds, sulfonium compounds, tertiary amines, metal hydroxides, metal alkoxides, and the like.

Suitable quaternary ammonium catalysts include, for example, tetramethyl ammonium chloride, benzyl trimethyl ammonium chloride, triethanol ammonium chloride, tetraethanol ammonium hydroxide, dodecyl dimethylbenzyl ammonium naphthenate and the like.

Suitable phosphonium catalysts include, for example, those quaternary phosphonium compounds disclosed in U.S. Pat. Nos. 3,948,855; 3,477,990 and 3,341,580 and Canadian No. 858,648 all of which are incorporated herein by reference. Particularly suitable such catalysts include, for example, ethyl triphenyl phosphonium iodide, ethyl triphenyl phosphonium bicarbonate, ethyl triphenyl phosphonium acetate.acetic acid complex, benzyl triphenyl phosphonium chloride, tetrabutyl phosphonium chloride, benzyl trimethyl ammonium chloride mixtures thereof and the like.

Suitable sulfonium catalysts include thiourea catalysts such as, for example, tetramethyl thiourea; N,N'-dimethyl thiourea; N,N'-diphenyl thiourea; mixtures thereof and the like as well as thiodiethanol and other sulfonium precursors.

Suitable tertiary amines include, for example, diethylenetriamine, N-methylmorpholine, triethylamine, tributylamine, benzyldimethylamine, tris(dimethylaminomethyl)phenol, mixtures thereof and the like.

Also suitable as catalysts are the basic ion exchange resins such as, for example, DOWEX MSA-1, DOWEX 11, DOWEX SBR, mixtures thereof and the like.

Although it is not necessary, the reaction is preferably conducted in the presence of an inert diluent or solvent such as, for example, alcohols, glycol ethers, ketones, mixtures thereof and the like.

Particularly suitable solvents or diluents include, for example, ethylene glycol monomethylether, ethylene glycol, monoethylether, ethylene glycol monobutylether, isopropyl alcohol, butyl alcohol, mixtures thereof and the like.

The reaction between the phosphoramide compound and the epihalohydrin can be conducted at a temperature of from about 25° C. to about 160° C., preferably from about 50° C. to about 120° C., and at a pressure of from about 20 mm of Hg to about 6000 mm of Hg, preferably from about 80 mm of Hg to about 760 mm of Hg for a time sufficient to complete the reaction to the degree desired. The actual time varies with temperature and pressure, but usually times of from about 30 min. (1800 s) to about 48 hours (172800 s) is sufficient.

The dehydrohalogenation can be accomplished with basic acting materials including alkali metal hydroxides, carbonates, aluminates, silicates, zincates and the like. Particularly suitable are, for example, sodium hydroxide, potassium hydroxide, sodium carbonate, mixtures thereof and the like.

The dehydrohalogenation reaction can be conducted at temperatures of from about 25° C. to about 120° C., preferably from about 40° C. to about 80° C., and at a pressure of from about 20 mm of Hg to about 760 mm of Hg, preferably from about 50 mm of Hg to about 300 mm of Hg for a time sufficient to complete the reaction to the degree desired. The actual time varies with temperature and pressure, but usually times of from about 30 min. (1800 s) to about 6 hours (21600 s) is sufficient.

The reactants are employed in quantities which provide a ratio of equivalents of epihalohydrin to equivalents of active hydrogens on the phosphoramide compound of from about 2:1 to about 12:1, preferably from about 4:1 to about 6:1; a ratio of equivalents of catalyst to equivalent of active hydrogens on the phosphoramide compound of from about 0:1 to about 0.5:1, preferably from about 0.01:1 to about 0.1:1; a quantity of solvent of from about 0 to about 50, preferably from about 20 to about 40% by weight of the quantity of epihalohydrin employed; and the dehydrohalogenation agent is employed in a quantity which provides a ratio of equivalents of dehydrohalogenating agent to equivalent of active hydrogen atom on the phosphoramide compound of from about 0.9:1 to about 3:1, preferably from about 1.1:1 to about 2:1.

The epoxy resins of the present invention can be cured with any of the known curing agents such as, for example, primary amines, acids, acid anhydrides, biguanides, secondary amines, tertiary amines, Lewis Acids, mixtures thereof and the like. Particularly suitable curing agents include, for example, methylene dianiline, ethylene diamine, diethylene triamine, triethylene tetramine, diaminodiphenyl sulfone, nadicmethyl anhydride, dicyanamide, 2-methyl imidazol, mixtures thereof and the like.

The compositions of the present invention are useful in the preparation of castings, laminates, coatings and the like.

In addition to the epoxy resin and curing agent, the compositions can contain pigments, dyes, fillers, flow control agents, solvents, rubber modifiers, combinations thereof and the like.

The following examples are illustrative of the present invention but are not to be construed as to limiting the scope thereof in any manner.

EXAMPLE 1

N,N',N''-triphenylphosphoramide (21.54 g), 111.0 g of epichlorohydrin, and 0.74 g of benzyl trimethylammonium chloride were heated at 120° C. for one hour (3600 s). The solution was then cooled to 65° C., and 47.6 g of ethylene glycol monomethylether (available from The Dow Chemical Company as DOWANOL® PM), and 1.6 g of water were added. This solution was then heated at 65° C. under approximately 180 mm of Hg pressure such as to give a gentle distillation. The reaction vessel was fitted with a device such that the distillate could be separated into two layers, and the heavier bottom layer recycled to the reaction. Sodium hydroxide (32 g of 50% aqueous solution) was slowly added during approximately 4½ hours (16200 s), then cooled and the salt removed via filtration. The excess epichlorohydrin and solvent were removed by vacuum distillation at 100° C. and about 1 mm of Hg pressure. The resinous product was a viscous semisolid at ambient temperature. It had an epoxide content of 17.3% (EEW = ~249), and a hydrolyzable chloride content of 0.13%.

EXAMPLE 2

N,N',N''-tributylphosphoramide (17.56 g), 92.5 g of epichlorohydrin, and 0.37 g of benzyl trimethylammonium chloride were heated at 50° C. for 24 hours (86400 s), then at 90° C. for an additional 5 hours (18000 s). The solution was then cooled to 65° C. and 49.8 g of isopropanol and 8.0 g of water was added. Sodium hydroxide (36 g of a 20% aqueous solution) was slowly added during approximately 45 minutes (2700 s), then digested at 65° C. for an additional 15 minutes (900 s). The aqueous layer was then separated, and an additional 16 g of 20% aqueous sodium hydroxide was added during approximately 15–20 minutes (900 1200 s), then digested for an additional 15 minutes (900 s). The mixture was then cooled to 25° C. The aqueous layer separated, and the organic phase washed with excess water till free of salt and sodium hydroxide. The excess epichlorohydrin and solvent were then removed via vacuum distillation at 100° C. and approximately 1 mm Hg pressure. The product was a viscous liquid with an epoxy content of 15.8% (EEW = ~272).

I claim:

1. An epoxy resin which results from dehydrohalogenating the reaction product of an excess of at least one epihalohydrin with at least one phosphoramide compound represented by the formula

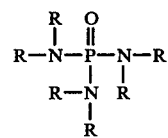

wherein each R is independently hydrogen or a hydrocarbyl or an inert substituted hydrocarbyl group having from 1 to about 20 carbon atoms with the proviso that at least 2 of the R groups are hydrogen and removing the excess epihalohydrin.

2. An epoxy resin of claim 1 wherein each R is independently hydrogen or a hydrocarbyl or substituted hydrocarbyl group having from 1 to about 10 carbon atoms and said epihalohydrin is epichlorohydrin.

3. An epoxy resin of claim 2 wherein each R is independently hydrogen, methyl, ethyl, propyl, butyl or phenyl with the proviso that at least 3 of the R groups are hydrogen.

4. An epoxy resin of claim 3 wherein each R is independently hydrogen, butyl or phenyl.

5. An epoxy resin represented by the formula

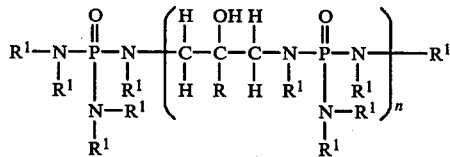

wherein each R is independently hydrogen or an alkyl group having from about 1 to about 4 carbon atoms; each $R^1$ is independently a hydrocarbyl or an inert substituted hydrocarbyl group having from 1 to about 20 carbon atoms or

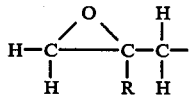

with the proviso that at least two of the $R^1$ groups are

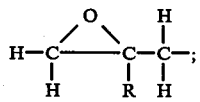

and n has an average value of from zero to about 10.

6. An epoxy resin of claim 5 wherein each R is hydrogen, each $R^1$ is independently a hydrocarbyl or an inert substituted hydrocarbyl group having from 1 to about 10 carbon atoms or

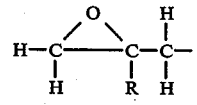

with the proviso that at least two of the $R^1$ groups are

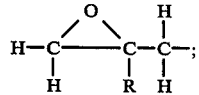

and n has an average value of from zero to about 2.

7. An epoxy resin of claim 6 wherein each $R^1$ is independently methyl, ethyl, propyl, butyl, phenyl or

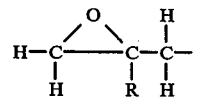

with the proviso that at least 3 of the $R^1$ groups are

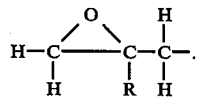.

8. An epoxy resin of claim 7 wherein each $R^1$ is independently butyl, phenyl or

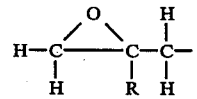

with the proviso that at least 3 of the $R^1$ groups are

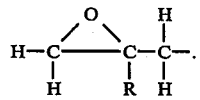.

9. A curable composition comprising (1) an epoxy resin of claims 1, 2, 3, 4, 5, 6, 7 or 8 and (2) a curing quantity of a suitable curing agent and/or catalyst.

10. A product resulting from curing a composition of claim 9.

* * * * *